United States Patent
Baba et al.

(10) Patent No.: US 11,136,569 B2
(45) Date of Patent: Oct. 5, 2021

(54) HEAT RESISTANT ISOAMYLASE

(71) Applicant: GODO SHUSEI CO., LTD., Chuo-ku (JP)

(72) Inventors: Masahiro Baba, Matsudo (JP); Ryoko Sano, Matsudo (JP); Shun Ogawa, Matsudo (JP); Hirofumi Horiguchi, Matsudo (JP); Jun Yoshikawa, Matsudo (JP)

(73) Assignee: GODO SHUSEI CO., LTD., Chuo-ku (JP)

( * ) Notice: Subject to any disclaimer, the term of this patent is extended or adjusted under 35 U.S.C. 154(b) by 182 days.

(21) Appl. No.: 16/301,325

(22) PCT Filed: May 26, 2017

(86) PCT No.: PCT/JP2017/019635
§ 371 (c)(1),
(2) Date: Nov. 13, 2018

(87) PCT Pub. No.: WO2017/204317
PCT Pub. Date: Nov. 30, 2017

(65) Prior Publication Data
US 2020/0291371 A1 Sep. 17, 2020

(30) Foreign Application Priority Data

May 27, 2016 (JP) .............................. JP2016-106198

(51) Int. Cl.
*C12N 9/44* (2006.01)

(52) U.S. Cl.
CPC ...... *C12N 9/246* (2013.01); *C12Y 302/01068* (2013.01)

(58) Field of Classification Search
CPC .......... C12N 9/246; C12N 15/09; C12N 5/10; C12Y 302/01068
See application file for complete search history.

(56) References Cited

U.S. PATENT DOCUMENTS

| | | | |
|---|---|---|---|
| 5,750,876 A * | 5/1998 | Barry ................... | C12N 9/1241 435/101 |
| 6,087,149 A | 7/2000 | Tsutsumi et al. | |
| 8,409,830 B2 | 4/2013 | Hoff et al. | |
| 9,005,681 B2 | 4/2015 | Ichihara et al. | |
| 2002/0081670 A1 | 6/2002 | Bisgard-Frantzen et al. | |
| 2011/0045136 A1 | 2/2011 | Hoff et al. | |
| 2013/0022711 A1 | 1/2013 | Ichihara et al. | |
| 2013/0089897 A1 | 4/2013 | Hoff et al. | |
| 2014/0038242 A1 | 2/2014 | Hoff et al. | |
| 2014/0045223 A1 | 2/2014 | Hoff et al. | |

FOREIGN PATENT DOCUMENTS

| | | |
|---|---|---|
| JP | 2002-517157 A | 6/2002 |
| JP | 2002-519054 A | 7/2002 |
| WO | WO 1996/03513 A2 * | 2/1996 |

OTHER PUBLICATIONS

Whisstock et al. Quaterly Reviews of Biophysics, "Prediction of protein function from protein sequence and structure", 36(3): 307-340, 2003.*
Witkowski et al. Conversion of a beta-ketoacyl synthase to a malonyl decarboxylase by replacement of the active-site cysteine with glutamine, Biochemistry. 38(36):11643-50, 1999.*
Chica et al., Semi-rational approaches to engineering enzyme activity: combining the benefits of directed evolution and rational design. Curr. Opi. Biotechnol. vol. 16: 378-384, 2005.*
Kisselev L., Polypeptide release factors in prokaryotes and eukaryotes: same function, different structure. Structure, vol. 10: 8-9, 2002.*
Extended European Search Report dated Dec. 5, 2019 in European Patent Application No. 17802903.9, 10 pages.
Database USPTO Proteins [Online] "Sequence 8 from U.S. Pat. No. 9,005,681", XP055643469, retrieved from EBI accession No. USPOP: AKX89694, Database accession No. AKX89694, Aug. 13, 2015, 1 page.
Database USPTO Proteins [Online] "Sequence 4 from U.S. Pat. No. 8,409,830", XP055643471, retrieved from EBI accession No. USPOP: AGM91721, Database accession No. AGM91721, May 30, 2013, 1 page.
International Search Report dated Aug. 15, 2017 in PCT/JP2017/019635 filed May 26, 2017.
Hizukuri, S. et al., "Properties of Flavobacterium odoratum KU Isoamylase," Starch, vol. 48, 1996, pp. 295-300.
Grandi, G. et al., "Stabilization of Industrial Enzymes by Protein Engineering," Protein Engineering in Industrial Biotechnology, 2000, pp. 147-157.
Tognoni, A. et al., "Cloning and Nucleotide Sequence of the Isoamylase Gene from a Strain of *Pseudomonas* sp.," Journal of General Microbiology, vol. 135, 1989, pp. 37-45.
Tachibana, A. et al., "Purification, Characterization and Crystal Structure of Isoamylase from Thermophilic Bacteria *Rhodothermus marinus*," Scientific Report of the Faculty of Agriculture, Okayama University, vol. 97, 2008, pp. 1-7 (with English abstract).

* cited by examiner

*Primary Examiner* — Iqbal H Chowdhury
(74) *Attorney, Agent, or Firm* — Oblon, McClelland, Maier & Neustadt, L.L.P.

(57) ABSTRACT

Provided are a novel isoamylase improved in optimum temperature, and more specifically, improved in heat resistance, and a process for producing the isoamylase.
An isoamylase having at least one amino acid mutation selected from the group consisting of D268A, M277I, A549P, A554P and A580T in an isoamylase consisting of an amino acid sequence represented by SEQ ID No: 1 or an isoamylase consisting of the amino acid sequence represented by SEQ ID No: 1 and having deletion, substitution or insertion of one to several amino acid residues.

6 Claims, 1 Drawing Sheet
Specification includes a Sequence Listing.

[Figure 1]

```
SEQUENCE LISTING

<160> NUMBER OF SEQ ID NOS: 5

<210> SEQ ID NO 1
<211> LENGTH: 776
<212> TYPE: PRT
<213> ORGANISM: Pseudomonas amyloderamosa

<400> SEQUENCE: 1

Met Lys Cys Pro Lys Ile Leu Ala Ala Leu Leu Gly Cys Ala Val Leu
1               5                   10                  15

Ala Gly Val Pro Ala Met Pro Ala His Ala Ala Ile Asn Ser Met Ser
                20                  25                  30

Leu Gly Ala Ser Tyr Asp Ala Gln Gln Ala Asn Ile Thr Phe Arg Val
            35                  40                  45

Tyr Ser Ser Gln Ala Thr Arg Ile Val Leu Tyr Leu Tyr Ser Ala Gly
    50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
                85                  90                  95

Ile Thr Gly Ala Val Tyr Tyr Gly Tyr Arg Ala Trp Gly Pro Asn Trp
            100                 105                 110
```

-continued

Pro Tyr Ala Ser Asn Trp Gly Lys Gly Ser Gln Ala Gly Phe Val Ser
         115                 120                 125

Asp Val Asp Ala Asn Gly Asp Arg Phe Asn Pro Asn Lys Leu Leu Leu
130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Gly Ala Ser Tyr Arg Thr Thr Asp
                165                 170                 175

Ser Gly Ile Tyr Ala Pro Lys Gly Val Leu Val Pro Ser Thr Gln
                180                 185                 190

Ser Thr Gly Thr Lys Pro Thr Arg Ala Gln Lys Asp Asp Val Ile Tyr
        195                 200                 205

Glu Val His Val Arg Gly Phe Thr Glu Gln Asp Thr Ser Ile Pro Ala
        210                 215                 220

Gln Tyr Arg Gly Thr Tyr Tyr Gly Ala Gly Leu Lys Ala Ser Tyr Leu
225                 230                 235                 240

Ala Ser Leu Gly Val Thr Ala Val Glu Phe Leu Pro Val Gln Glu Thr
                245                 250                 255

Gln Asn Asp Ala Asn Asp Val Val Pro Asn Ser Asp Ala Asn Gln Asn
            260                 265                 270

Tyr Trp Gly Tyr Met Thr Glu Asn Tyr Phe Ser Pro Asp Arg Arg Tyr
        275                 280                 285

Ala Tyr Asn Lys Ala Ala Gly Gly Pro Thr Ala Glu Phe Gln Ala Met
        290                 295                 300

Val Gln Ala Phe His Asn Ala Gly Ile Lys Val Tyr Met Asp Val Val
305                 310                 315                 320

Tyr Asn His Thr Ala Glu Gly Gly Thr Trp Thr Ser Ser Asp Pro Thr
                325                 330                 335

Thr Ala Thr Ile Tyr Ser Trp Arg Gly Leu Asp Asn Ala Thr Tyr Tyr
            340                 345                 350

Glu Leu Thr Ser Gly Asn Gln Tyr Phe Tyr Asp Asn Thr Gly Ile Gly
        355                 360                 365

Ala Asn Phe Asn Thr Tyr Asn Thr Val Ala Gln Asn Leu Ile Val Asp
        370                 375                 380

Ser Leu Ala Tyr Trp Ala Asn Thr Met Gly Val Asp Gly Phe Arg Phe
385                 390                 395                 400

Asp Leu Ala Ser Val Leu Gly Asn Ser Cys Leu Asn Gly Ala Tyr Thr
                405                 410                 415

Ala Ser Ala Pro Asn Cys Pro Asn Gly Gly Tyr Asn Phe Asp Ala Ala
            420                 425                 430

Asp Ser Asn Val Ala Ile Asn Arg Ile Leu Arg Glu Phe Thr Val Arg
        435                 440                 445

Pro Ala Ala Gly Gly Ser Gly Leu Asp Leu Phe Ala Glu Pro Trp Ala
450                 455                 460

Ile Gly Gly Asn Ser Tyr Gln Leu Gly Gly Phe Pro Gln Gly Trp Ser
465                 470                 475                 480

Glu Trp Asn Gly Leu Phe Arg Asp Ser Leu Arg Gln Ala Gln Asn Glu
                485                 490                 495

Leu Gly Ser Met Thr Ile Tyr Val Thr Gln Asp Ala Asn Asp Phe Ser
            500                 505                 510

Gly Ser Ser Asn Leu Phe Gln Ser Ser Gly Arg Ser Pro Trp Asn Ser
        515                 520                 525

Ile Asn Phe Ile Asp Val His Asp Gly Met Thr Leu Lys Asp Val Tyr

```
                  530                 535                 540
Ser Cys Asn Gly Ala Asn Asn Ser Gln Ala Trp Pro Tyr Gly Pro Ser
545                 550                 555                 560

Asp Gly Gly Thr Ser Thr Asn Tyr Ser Trp Asp Gln Gly Met Ser Ala
                565                 570                 575

Gly Thr Gly Ala Ala Val Asp Gln Arg Arg Ala Ala Arg Thr Gly Met
                580                 585                 590

Ala Phe Glu Met Leu Ser Ala Gly Thr Pro Leu Met Gln Gly Gly Asp
                595                 600                 605

Glu Tyr Leu Arg Thr Leu Gln Cys Asn Asn Ala Tyr Asn Leu Asp
        610                 615                 620

Ser Ser Ala Asn Trp Leu Thr Tyr Ser Trp Thr Thr Asp Gln Ser Asn
625                 630                 635                 640

Phe Tyr Thr Phe Ala Gln Arg Leu Ile Ala Phe Arg Lys Ala His Pro
                645                 650                 655

Ala Leu Arg Pro Ser Ser Trp Tyr Ser Gly Ser Gln Leu Thr Trp Tyr
                660                 665                 670

Gln Pro Ser Gly Ala Val Ala Asp Ser Asn Tyr Trp Asn Asn Thr Ser
        675                 680                 685

Asn Tyr Ala Ile Ala Tyr Ala Ile Asn Gly Pro Ser Leu Gly Asp Ser
        690                 695                 700

Asn Ser Ile Tyr Val Ala Tyr Asn Gly Trp Ser Ser Val Thr Phe
705                 710                 715                 720

Thr Leu Pro Ala Pro Pro Ser Gly Thr Gln Trp Tyr Arg Val Thr Asp
                725                 730                 735

Thr Cys Asp Trp Asn Asp Gly Ala Ser Thr Phe Val Ala Pro Gly Ser
                740                 745                 750

Glu Thr Leu Ile Gly Gly Ala Gly Thr Thr Tyr Gly Gln Cys Gly Gln
                755                 760                 765

Ser Leu Leu Leu Leu Ile Ser Lys
        770                 775
```

<210> SEQ ID NO 2  
<211> LENGTH: 30  
<212> TYPE: DNA  
<213> ORGANISM: Artificial Sequence  
<220> FEATURE:  
<223> OTHER INFORMATION: Synthetic primer

<400> SEQUENCE: 2
aaactgcaga tgaagtgccc aaagattctc          30

<210> SEQ ID NO 3  
<211> LENGTH: 30  
<212> TYPE: DNA  
<213> ORGANISM: Artificial Sequence  
<220> FEATURE:  
<223> OTHER INFORMATION: Synthetic primer

<400> SEQUENCE: 3
cccaagcttc tacttggaga tcaacagcag          30

<210> SEQ ID NO 4  
<211> LENGTH: 776  
<212> TYPE: PRT  
<213> ORGANISM: Pseudomonas amyloderamosa

<400> SEQUENCE: 4

-continued

```
Met Lys Cys Pro Lys Ile Leu Ala Ala Leu Leu Gly Cys Ala Val Leu
1               5                   10                  15

Ala Gly Val Pro Ala Met Pro Ala His Ala Ala Ile Asn Ser Met Ser
            20                  25                  30

Leu Gly Ala Ser Tyr Asp Ala Gln Gln Ala Asn Ile Thr Phe Arg Val
            35                  40                  45

Tyr Ser Ser Gln Ala Thr Arg Ile Val Leu Tyr Leu Tyr Ser Ala Gly
50                  55                  60

Tyr Gly Val Gln Glu Ser Ala Thr Tyr Thr Leu Ser Pro Ala Gly Ser
65                  70                  75                  80

Gly Val Trp Ala Val Thr Val Pro Val Ser Ser Ile Lys Ala Ala Gly
            85                  90                  95

Ile Thr Gly Ala Val Tyr Tyr Gly Tyr Arg Ala Trp Gly Pro Asn Trp
            100                 105                 110

Pro Tyr Ala Ser Asn Trp Gly Lys Gly Ser Gln Ala Gly Phe Val Ser
            115                 120                 125

Asp Val Asp Ala Asn Gly Asp Arg Phe Asn Pro Asn Lys Leu Leu Leu
            130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Gly Ala Ser Tyr Arg Thr Thr Asp
            165                 170                 175

Ser Gly Ile Tyr Ala Pro Lys Gly Val Val Leu Val Pro Ser Thr Gln
            180                 185                 190

Ser Thr Gly Thr Lys Pro Thr Arg Ala Gln Lys Asp Asp Val Ile Tyr
            195                 200                 205

Glu Val His Val Arg Gly Phe Thr Glu Gln Asp Thr Ser Ile Pro Ala
            210                 215                 220

Gln Tyr Arg Gly Thr Tyr Tyr Gly Ala Gly Leu Lys Ala Ser Tyr Leu
225                 230                 235                 240

Ala Ser Leu Gly Val Thr Ala Val Glu Phe Leu Pro Val Gln Glu Thr
            245                 250                 255

Gln Asn Asp Ala Asn Asp Val Val Pro Asn Ser Ala Ala Asn Gln Asn
            260                 265                 270

Tyr Trp Gly Tyr Ile Thr Glu Asn Tyr Phe Ser Pro Asp Arg Arg Tyr
            275                 280                 285

Ala Tyr Asn Lys Ala Ala Gly Gly Pro Thr Ala Glu Phe Gln Ala Met
            290                 295                 300

Val Gln Ala Phe His Asn Ala Gly Ile Lys Val Tyr Met Asp Val Val
305                 310                 315                 320

Tyr Asn His Thr Ala Glu Gly Gly Thr Trp Thr Ser Ser Asp Pro Thr
            325                 330                 335

Thr Ala Thr Ile Tyr Ser Trp Arg Gly Leu Asp Asn Ala Thr Tyr Tyr
            340                 345                 350

Glu Leu Thr Ser Gly Asn Gln Tyr Phe Tyr Asp Asn Thr Gly Ile Gly
            355                 360                 365

Ala Asn Phe Asn Thr Tyr Asn Thr Val Ala Gln Asn Leu Ile Val Asp
            370                 375                 380

Ser Leu Ala Tyr Trp Ala Asn Thr Met Gly Val Asp Gly Phe Arg Phe
385                 390                 395                 400

Asp Leu Ala Ser Val Leu Gly Asn Ser Cys Leu Asn Gly Ala Tyr Thr
            405                 410                 415

Ala Ser Ala Pro Asn Cys Pro Asn Gly Gly Tyr Asn Phe Asp Ala Ala
```

```
                    420              425              430
Asp Ser Asn Val Ala Ile Asn Arg Ile Leu Arg Glu Phe Thr Val Arg
            435                  440                  445

Pro Ala Ala Gly Gly Ser Gly Leu Asp Leu Phe Ala Glu Pro Trp Ala
            450                  455                  460

Ile Gly Gly Asn Ser Tyr Gln Leu Gly Gly Phe Pro Gln Gly Trp Ser
465                  470                  475                  480

Glu Trp Asn Gly Leu Phe Arg Asp Ser Leu Arg Gln Ala Gln Asn Glu
                485                  490                  495

Leu Gly Ser Met Thr Ile Tyr Val Thr Gln Asp Ala Asn Asp Phe Ser
                500                  505                  510

Gly Ser Ser Asn Leu Phe Gln Ser Ser Gly Arg Ser Pro Trp Asn Ser
                515                  520                  525

Ile Asn Phe Ile Asp Val His Asp Gly Met Thr Leu Lys Asp Val Tyr
                530                  535                  540

Ser Cys Asn Gly Pro Asn Asn Ser Gln Pro Trp Pro Tyr Gly Pro Ser
545                  550                  555                  560

Asp Gly Gly Thr Ser Thr Asn Tyr Ser Trp Asp Gln Gly Met Ser Ala
                565                  570                  575

Gly Thr Gly Ala Ala Val Asp Gln Arg Arg Ala Ala Arg Thr Gly Met
                580                  585                  590

Ala Phe Glu Met Leu Ser Ala Gly Thr Pro Leu Met Gln Gly Gly Asp
                595                  600                  605

Glu Tyr Leu Arg Thr Leu Gln Cys Asn Asn Asn Ala Tyr Asn Leu Asp
                610                  615                  620

Ser Ser Ala Asn Trp Leu Thr Tyr Ser Trp Thr Thr Asp Gln Ser Asn
625                  630                  635                  640

Phe Tyr Thr Phe Ala Gln Arg Leu Ile Ala Phe Arg Lys Ala His Pro
                645                  650                  655

Ala Leu Arg Pro Ser Ser Trp Tyr Ser Gly Ser Gln Leu Thr Trp Tyr
                660                  665                  670

Gln Pro Ser Gly Ala Val Ala Asp Ser Asn Tyr Trp Asn Asn Thr Ser
                675                  680                  685

Asn Tyr Ala Ile Ala Tyr Ala Ile Asn Gly Pro Ser Leu Gly Asp Ser
                690                  695                  700

Asn Ser Ile Tyr Val Ala Tyr Asn Gly Trp Ser Ser Val Thr Phe
705                  710                  715                  720

Thr Leu Pro Ala Pro Pro Ser Gly Thr Gln Trp Tyr Arg Val Thr Asp
                725                  730                  735

Thr Cys Asp Trp Asn Asp Gly Ala Ser Thr Phe Val Ala Pro Gly Ser
                740                  745                  750

Glu Thr Leu Ile Gly Gly Ala Gly Thr Thr Tyr Gly Gln Cys Gly Gln
                755                  760                  765

Ser Leu Leu Leu Leu Ile Ser Lys
                770                  775

<210> SEQ ID NO 5
<211> LENGTH: 776
<212> TYPE: PRT
<213> ORGANISM: Pseudomonas amyloderamosa

<400> SEQUENCE: 5

Met Lys Cys Pro Lys Ile Leu Ala Ala Leu Leu Gly Cys Ala Val Leu
1               5                   10                  15
```

Ala Gly Val Pro Ala Met Pro Ala His Ala Ala Ile Asn Ser Met Ser
             20                  25                  30

Leu Gly Ala Ser Tyr Asp Ala Gln Gln Ala Asn Ile Thr Phe Arg Val
         35                  40                  45

Tyr Ser Ser Gln Ala Thr Arg Ile Val Leu Tyr Leu Tyr Ser Ala Gly
 50                  55                  60

Tyr Gly Val Gln Glu Ser Ala Thr Tyr Thr Leu Ser Pro Ala Gly Ser
 65                  70                  75                  80

Gly Val Trp Ala Val Thr Val Pro Val Ser Ser Ile Lys Ala Ala Gly
             85                  90                  95

Ile Thr Gly Ala Val Tyr Gly Tyr Arg Ala Trp Gly Pro Asn Trp
             100                 105                 110

Pro Tyr Ala Ser Asn Trp Gly Lys Gly Ser Gln Ala Gly Phe Val Ser
             115                 120                 125

Asp Val Asp Ala Asn Gly Asp Arg Phe Asn Pro Asn Lys Leu Leu Leu
             130                 135                 140

Asp Pro Tyr Ala Gln Glu Val Ser Gln Asp Pro Leu Asn Pro Ser Asn
145                 150                 155                 160

Gln Asn Gly Asn Val Phe Ala Ser Gly Ala Ser Tyr Arg Thr Thr Asp
             165                 170                 175

Ser Gly Ile Tyr Ala Pro Lys Gly Val Val Leu Val Pro Ser Thr Gln
             180                 185                 190

Ser Thr Gly Thr Lys Pro Thr Arg Ala Gln Lys Asp Asp Val Ile Tyr
             195                 200                 205

Glu Val His Val Arg Gly Phe Thr Glu Gln Asp Thr Ser Ile Pro Ala
210                 215                 220

Gln Tyr Arg Gly Thr Tyr Tyr Gly Ala Gly Leu Lys Ala Ser Tyr Leu
225                 230                 235                 240

Ala Ser Leu Gly Val Thr Ala Val Glu Phe Leu Pro Val Gln Glu Thr
             245                 250                 255

Gln Asn Asp Ala Asn Asp Val Val Pro Asn Ser Ala Ala Asn Gln Asn
             260                 265                 270

Tyr Trp Gly Tyr Ile Thr Glu Asn Tyr Phe Ser Pro Asp Arg Arg Tyr
             275                 280                 285

Ala Tyr Asn Lys Ala Ala Gly Gly Pro Thr Ala Glu Phe Gln Ala Met
             290                 295                 300

Val Gln Ala Phe His Asn Ala Gly Ile Lys Val Tyr Met Asp Val Val
305                 310                 315                 320

Tyr Asn His Thr Ala Glu Gly Gly Thr Trp Thr Ser Ser Asp Pro Thr
             325                 330                 335

Thr Ala Thr Ile Tyr Ser Trp Arg Gly Leu Asp Asn Ala Thr Tyr Tyr
             340                 345                 350

Glu Leu Thr Ser Gly Asn Gln Tyr Phe Tyr Asp Asn Thr Gly Ile Gly
             355                 360                 365

Ala Asn Phe Asn Thr Tyr Asn Thr Val Ala Gln Asn Leu Ile Val Asp
             370                 375                 380

Ser Leu Ala Tyr Trp Ala Asn Thr Met Gly Val Asp Gly Phe Arg Phe
385                 390                 395                 400

Asp Leu Ala Ser Val Leu Gly Asn Ser Cys Leu Asn Gly Ala Tyr Thr
             405                 410                 415

Ala Ser Ala Pro Asn Cys Pro Asn Gly Gly Tyr Asn Phe Asp Ala Ala
             420                 425                 430

Asp Ser Asn Val Ala Ile Asn Arg Ile Leu Arg Glu Phe Thr Val Arg

```
                435                 440                 445
Pro Ala Ala Gly Gly Ser Gly Leu Asp Leu Phe Ala Glu Pro Trp Ala
    450                 455                 460
Ile Gly Gly Asn Ser Tyr Gln Leu Gly Gly Phe Pro Gln Gly Trp Ser
465                 470                 475                 480
Glu Trp Asn Gly Leu Phe Arg Asp Ser Leu Arg Gln Ala Gln Asn Glu
                    485                 490                 495
Leu Gly Ser Met Thr Ile Tyr Val Thr Gln Asp Ala Asn Asp Phe Ser
            500                 505                 510
Gly Ser Ser Asn Leu Phe Gln Ser Ser Gly Arg Ser Pro Trp Asn Ser
        515                 520                 525
Ile Asn Phe Ile Asp Val His Asp Gly Met Thr Leu Lys Asp Val Tyr
    530                 535                 540
Ser Cys Asn Gly Pro Asn Asn Ser Gln Pro Trp Pro Tyr Gly Pro Ser
545                 550                 555                 560
Asp Gly Gly Thr Ser Thr Asn Tyr Ser Trp Asp Gln Gly Met Ser Ala
                565                 570                 575
Gly Thr Gly Thr Ala Val Asp Gln Arg Arg Ala Ala Arg Thr Gly Met
            580                 585                 590
Ala Phe Glu Met Leu Ser Ala Gly Thr Pro Leu Met Gln Gly Gly Asp
        595                 600                 605
Glu Tyr Leu Arg Thr Leu Gln Cys Asn Asn Asn Ala Tyr Asn Leu Asp
    610                 615                 620
Ser Ser Ala Asn Trp Leu Thr Tyr Ser Trp Thr Thr Asp Gln Ser Asn
625                 630                 635                 640
Phe Tyr Thr Phe Ala Gln Arg Leu Ile Ala Phe Arg Lys Ala His Pro
                645                 650                 655
Ala Leu Arg Pro Ser Ser Trp Tyr Ser Gly Ser Gln Leu Thr Trp Tyr
            660                 665                 670
Gln Pro Ser Gly Ala Val Ala Asp Ser Asn Tyr Trp Asn Asn Thr Ser
        675                 680                 685
Asn Tyr Ala Ile Ala Tyr Ala Ile Asn Gly Pro Ser Leu Gly Asp Ser
    690                 695                 700
Asn Ser Ile Tyr Val Ala Tyr Asn Gly Trp Ser Ser Ser Val Thr Phe
705                 710                 715                 720
Thr Leu Pro Ala Pro Pro Ser Gly Thr Gln Trp Tyr Arg Val Thr Asp
                725                 730                 735
Thr Cys Asp Trp Asn Asp Gly Ala Ser Thr Phe Val Ala Pro Gly Ser
            740                 745                 750
Glu Thr Leu Ile Gly Gly Ala Gly Thr Thr Tyr Gly Gln Cys Gly Gln
        755                 760                 765
Ser Leu Leu Leu Leu Ile Ser Lys
    770                 775
```

HEAT RESISTANT ISOAMYLASE

FIELD OF THE INVENTION

The present invention relates to an isoamylase variant improved in heat resistance and a process for producing the isoamylase variant.

BACKGROUND OF THE INVENTION

In the saccharification industry, as an enzyme responsible for hydrolyzing an α-1,6-glucopyranoside bond of starch and amylopectin, pullulanase and isoamylase produced by e.g., *Klebsiella pneumoniae* are known. Among them, isoamylase is an enzyme responsible for hydrolyzing an α-1,6-glucopyranoside bond of starch, amylopectin and glycogen. It is known that since the reaction of isoamylase does not reversibly proceed, high-purity glucose and maltose can be produced if another type of amylase and glucoamylase are used. As a bacterium which produces isoamylase, e.g., *Pseudomonas amyloderamosa* (Non Patent Document 1), has been reported.

PRIOR ART DOCUMENT

Non Patent Document

[Nan Patent Document 1] Starch (1996), 48: 295-300

SUMMARY OF INVENTION

Problem to be Solved by the Invention

However, the optimum temperature of isoamylase produced by e.g., *Pseudomonas amyloderamosa* is lower than that of (another type of) amylase. Because of this, it has been difficult to apply such an isoamylase in combination with amylase in the range (level) of a reaction temperature industrially used.

Thus, an object of the present invention is to provide a novel isoamylase improved in optimum temperature, and more specifically, improved in heat resistance, and a process for producing the isoamylase.

Means for Solving the Problem

The present inventors produced a protein partially modified in the amino acid sequence of the isoamylase produced by e.g., *Pseudomonas amyloderamosa* and investigated the heat resistance thereof. As a result, the present inventors found that an isoamylase variant improved in heat resistance (increased in heatproof temperature by 5° C. to 10° C.) can be obtained by changing an amino acid(s) at a predetermined position(s) to another amino acid(s). Based on the finding, the present invention was accomplished.

More specifically, the present invention provides the following [1] to [10].

[1] An isoamylase comprising at least one amino acid mutation selected from the group consisting of D268A, M277I, A549P, A554P and A580T in an isoamylase consisting of an amino acid sequence represented by SEQ ID No: 1 or an isoamylase consisting of the amino acid sequence represented by SEQ ID No: 1 and having deletion, substitution or insertion of one to several amino acid residues.

[2] The isoamylase according to [1], wherein the amino acid mutation includes a double to quintuple mutation selected from the group consisting of D268A, M277I, A549P, A554P and A580T.

[3] The isoamylase according to [1] or [2], wherein the amino acid mutation includes a mutation selected from the group consisting of A554P, M277I, D268A, A580T, A554P/M277I, A554P/M277I/D268A, A554P/M277I/D268A/A549P and A554P/M277I/D268A/A549P/A580T.

[4] The isoamylase according to any one of [1] to [3], wherein the amino acid mutation includes a mutation selected from the group consisting of A554P/M277I, A554P/M277I/D268A, A554P/M277I/D268A/A549P and A554P/M277I/D268A/A549P/A580T.

[5] A gene encoding the isoamylase according to any one of [1] to [4].

[6] A recombinant vector comprising the gene according to [5].

[7] A transformant transformed with the recombinant vector according to [6].

[8] A process for producing an isoamylase comprising culturing the transformant according to [7] and recovering isoamylase from a culture.

[9] An enzyme composition for saccharification of starch comprising the isoamylase according to any one of [1] to [4].

[10] The enzyme composition for saccharification of starch according to [9], further comprising an enzyme selected from the group consisting of β-amylase, α-amylase and glucoamylase.

Effect of Invention

The isoamylase of the present invention is improved in heat resistance (increased in heatproof temperature by 5° C. or more) and the heatproof temperature overlaps with the optimum temperatures of other amylases. Accordingly, if the isoamylase of the present invention is used in combination with other amylases, to e.g., starch, high purity glucose, maltose and the like can be industrially advantageously produced. In the present invention, "used in combination" refers to the state where at least two enzymes are active in a mixture containing the isoamylase of the present invention and at least one enzyme other than the isoamylase.

MODE FOR CARRYING OUT THE INVENTION

The isoamylase of the present invention is an isoamylase having at least one amino acid mutation selected from the group consisting of D268A, M277I, A549P, A554P and A580T, in an isoamylase consisting of an amino acid sequence represented by SEQ ID No: 1 or an isoamylase consisting of the amino acid sequence represented by SEQ ID No: 1 and having deletion, substitution or insertion of one to several amino acid residues.

Here, the isoamylase consisting of an amino acid sequence represented by SEQ ID No: 1 is the isoamylase produced by *Pseudomonas amyloderamosa* described in Non Patent Document 1. Examples of the isoamylase may include an isoamylase not derived from *Pseudomonas amyloderamosa* as long as it has the same amino acid sequence, and also include not only a polypeptide but also a glycopeptide as long as it has the same amino acid sequence. Note that, SEQ ID No: 1 represents the amino acid sequence of a matured isoamylase protein.

In the isoamylase consisting of the amino acid sequence represented by SEQ ID No: 1 and having deletion, substitution or insertion of one to several amino acid residues, the number of amino acid residues constituting deletion, substitution or insertion is not particularly limited as long as the isoamylase expresses the same enzyme activity as the isoamylase consisting of the amino acid sequence represented by SEQ ID No: 1; however, the number is preferably 1 to 20, more preferably 1 to 10 and further preferably 1 to 8. The amino acid sequence identity of the isoamylase having deletion, substitution or insertion with the isoamylase of SEQ ID No: 1 is preferably 80% or more, more preferably 85% or more, further preferably 90% or more and further more preferably 95% or more. Such a sequence identity expressed by percentages can be computationally obtained by using released or commercially available software having an algorithm for comparing a sequence to a standard/reference sequence. For example, BLAST, FASTA or GENETYX (manufactured by GENETYX Co., Ltd.) can be used.

The isoamylase of the present invention has at least one amino acid mutation selected from the group consisting of D268A, M277I, A549P, A554P and A580T. More preferable amino acid mutation includes a double to quintuple mutation selected from the group consisting of D268A, M277I, A549P, A554P and A580T.

Specific examples of the amino acid mutation include A554P, M277I, D268A, A549P, A580T, A554P/M277I, A554P/D268A, A554P/A549P, A554P/A580T, M277I/D268A, M277I/A549P, M277I/A580T, D268A/A549P, D268A/A580T, A549P/A580T, A554P/M277I/D268A, A554P/M277I/A549P, A554P/M277I/A580T, A554P/D268A/A549P, A554P/D268A/A580T, A554P/A549P/A580T, M277I/D268A/A549P, M277I/D268A/A580T, D268A/A549P/A580T, A554P/M277I/D268A/A549P, A554P/D268A/A549P/A580T, A554P/M277I/A549P/A580T, A554P/M277I/D268A/A580T, M277I/D268A/A549P/A580T and A554P/M277I/D268A/A549P/A580T.

Examples of a further preferable amino acid mutation include A554P/M277I, A564P/M277I/D268A, A554P/M277I/D268A/A549P and A554P/M277I/D268A/A549P/A580T.

The isoamylase variant of the present invention can be produced by using a gene, which is constructed such that the isoamylase consisting of an amino acid sequence represented by SEQ ID No: or an isoamylase consisting of the amino acid sequence represented by SEQ ID No: and having deletion, substitution or insertion of one to several amino acid residues has at least one amino acid mutation selected from the group consisting of D268A, M277I, A549P, A554P and A580T.

A gene for producing an isoamylase variant of the present invention is a gene having a nucleotide sequence encoding an isoamylase variant as mentioned above and can be constructed, for example, by replacing, in a gene encoding the amino acid sequence represented by SEQ ID No: 1, the nucleotide sequence encoding the amino acid sequence to be replaced by a nucleotide encoding a desired amino acid residue. Various methods for such a site-specific nucleotide sequence substitution are well known in the art, for example, a PCR method using a properly designed primer(s) can be used. Alternatively, a gene encoding a modified amino acid sequence can be fully synthesized.

The gene thus obtained is inserted in an appropriate expression vector, which is further integrated into an appropriate host (for example, *Escherichia coli*) to transform the host. Many vectors/host systems for expressing an exogenous protein are known in the art. As an expression vector for integrating an isoamylase variant gene, a plasmid vector is mentioned. For example, pET-14b and pBR322 are mentioned for *E. coli*; e.g., pUB110 for *Bacillus subtilis*; e.g., pPTRI for a filamentous fungus; and e.g., pRS403 for a yeast.

The recombinant plasmid obtained is integrated in a microorganism such as *E. coli, Bacillus subtilis*, a mold, a yeast, *Actinomycete, Acetobacter* and *Pseudomonas* sp. to transform the microorganism. If the transformant thus obtained is cultured, an isoamylase variant of the present invention can be obtained. In the transformant, the gene for the isoamylase variant may be present in the plasmid or incorporated in the genome of the microorganism.

The isoamylase of the present invention is improved in heat resistance (increased in heatproof temperature by 5° C. to 10° C.) compared to the isoamylase produced by e.g., *Pseudomonas amyloderamosa* and has the same optimum pH and isoamylase activity as those of the isoamylase produced by e.g., *Pseudomonas amyloderamosa*. Accordingly, if an enzyme selected from the group consisting of β-amylase, α-amylase and glucoamylase is applied to starch in combination with the isoamylase of the present invention, high purity glucose and maltose can be easily obtained. As the β-amylase used herein, for example, GODO-GBA2 (GODO SHUSEI CO., LTD.), OPTIMALT BBA (Danisco Japan Ltd.), β-amylase L/R (Nagase ChemteX Corporation) and Hi-Maltosin GL (HBI Enzymes Inc.) can be used. As the α-amylase, for example, KLEISTASE T10 (Daiwa Fine Chemicals Co., Ltd) can be used. As the glucoamylase, for example, Gluczyme (Amano Enzyme Inc.) and GODO-ANGH (GODO SHUSEI CO., LTD.) can be used.

The isoamylase of the present invention is preferably used as the isoamylase for saccharification and further preferably as the isoamylase for saccharification of starch.

Preferably, the isoamylase of the present invention is, if necessary, mixed with at least one other enzyme and used as an enzyme composition for saccharification of starch. The at least one other enzyme can be selected from the group consisting of β-amylase, α-amylase and glucoamylase mentioned above.

The reaction is carried out, for example, by adding the aforementioned enzyme to starch and an enzyme for starch saccharification such as amylase, and mixing/stirring in the pH and temperature conditions where the enzyme acts. According to the process of the present invention, high purity glucose and maltose can be industrially advantageously produced.

EXAMPLES

Now, the present invention will be described in more detail by way of Examples; however, the present invention is not particularly limited to these.

Example 1

Site-Specific Mutagenesis of Isoamylase

Using the genome of *Pseudomonas amyloderamosa* as a template and PSTPIA-F (AAACTGCAGATGAAGTGCC-CAAAGATTCTC (SEQ ID No: 2)) and HINDPIA-R (CC-CAAGCTTCTACTTGGAGATCAACAGCAG (SEQ ID No: 3)) as primers, a fragment (about 2.3 kb) containing an acid-resistant isoamylase gene sequence was obtained. The fragment was digested with restriction enzymes Pst I and Hind III and ligated with a fragment (about 2.2 kb) of pHSG398 (Takara Bio Inc.) digested with restriction enzymes Pst I and Hind III to obtain p-PI. Plasmid p-PI, which is a plasmid expressing native acid-resistant isoamylase, was subjected to site-specific mutagenesis to obtain a single variant (A554P) expression plasmid, p-PIA554P. Similarly, a single variant (M277I) expression plasmid p-PIM277I, a single variant (D268A) expression plasmid, p-PID268A and a single variant (A580T) expression plasmid, p-PIA580T were obtained. In addition, p-PIA554P was subjected to site-specific mutagenesis to obtain a double variant (A554P/M277I) expression plasmid, p-PI2M, a triple variant (A554P/M277I/D268A) expression plasmid, p-PI3M, a quadruple variant (A554P/M277I/D268A/A549P) expression plasmid, p-PI4M and a quintuple variant (A554P/M277I/D268A/A549P/A580T) expression plasmid, p-PI5M.

Example 2

Production of Enzyme

E. coli DH5α strains were transformed separately with a native acid-resistant isoamylase expression plasmid, p-PI, a single variant (A554P) expression plasmid, p-PIA554P, a single variant (M277I) expression plasmid, p-PIM277I, a single variant (D268A) expression plasmid, p-PID268A, a single variant (A580T) expression plasmid, p-PIA580T, a double variant (A554P/M277I) expression plasmid, p-PI2M, a triple variant (A554P/M277I/D268A) expression plasmid, p-PI3M, quadruple variant (A554P/M277I/D268A/A549P) expression plasmid, p-PI4M and a quintuple variant (A554P/M277I/D268A/A549P/A580T) expression plasmid, p-PI5M, to obtain E. coli strains producing individual isoamylases. These E. coli strains were each cultured in an LB medium (yeast extract: 0.5%; tryptone: 1.0%; sodium chloride: 0.5%; IPTG: 0.1 mM, pH 7.2) containing a 30 μg/mL chloramphenicol, at 30° C. for 3 days to obtain a culture solution (1 L). The bacterium cells were ultrasonically crushed and centrifuged (10,000 g, 10 minutes). The supernatants were subjected to UF concentration (AIP module, manufactured by Asahi Kasei Corporation) so as to obtain a concentration of 1,000 U/mL. These concentrated supernatants were sterilized by a membrane having a pore size of 0.2 μm to separately obtain enzyme solutions of a native acid-resistant isoamylase, a single variant (A554P) isoamylase, a single variant (M277I) isoamylase, a single variant (D268A) isoamylase, a single variant (A580T) isoamylase, a double variant (A554P/M277I) isoamylase, a triple variant (A554P/M277I/D268A) isoamylase, a quadruple variant (A554P/M277I/D268A/A549P) isoamylase and a quintuple variant (A554P/M277I/D268A/A549P/A580T) isoamylase.

Example 3

Improvement of Thermal Stability of Individual Variants

These enzyme solutions were kept at 40° C., 50° C., 55° C., 57.5° C., 60° C., 62.5° C., or 65° C. for 10 minutes, ice-cooled and the residual activity was measured. Using an approximate expression, which was prepared by plotting residual activity at individual temperatures, the temperature corresponding to a residual activity of 50% was computationally obtained and compared to that of the native acid-resistant isoamylase. A degree of an increase was determined as the degree of heat resistance. The amino acid sequence of the quadruple variant is represented by SEQ ID No: 4. The amino acid sequence of the quintuple variant is represented by SEQ ID No: 5.

<Method for Measuring Activity>

A method for measuring the activity of isoamylase is as follows:

With a 0.5% waxy cornstarch solution (0.35 mL), a 0.5 M acetate buffer, pH 4.5 (0.1 mL) was mixed and a diluted enzyme solution (0.1 mL) was added at an appropriate time. The mixture was allowed to react at 45° C. for 15 minutes. Thereafter, an iodide solution (0.5 M potassium iodide solution containing 0.05 M iodine) (0.5 mL) diluted 5 fold with 0.1 N HCl was added to terminate the enzyme reaction. After water (10 mL) was added to the reaction solution and the mixture was sufficiently stirred, absorbance was measured at 610 nm by a spectrophotometer. The enzyme activity is represented by the unit, which is the amount of enzyme increasing 0.01 absorbance per minute in the above conditions.

Figure 1:
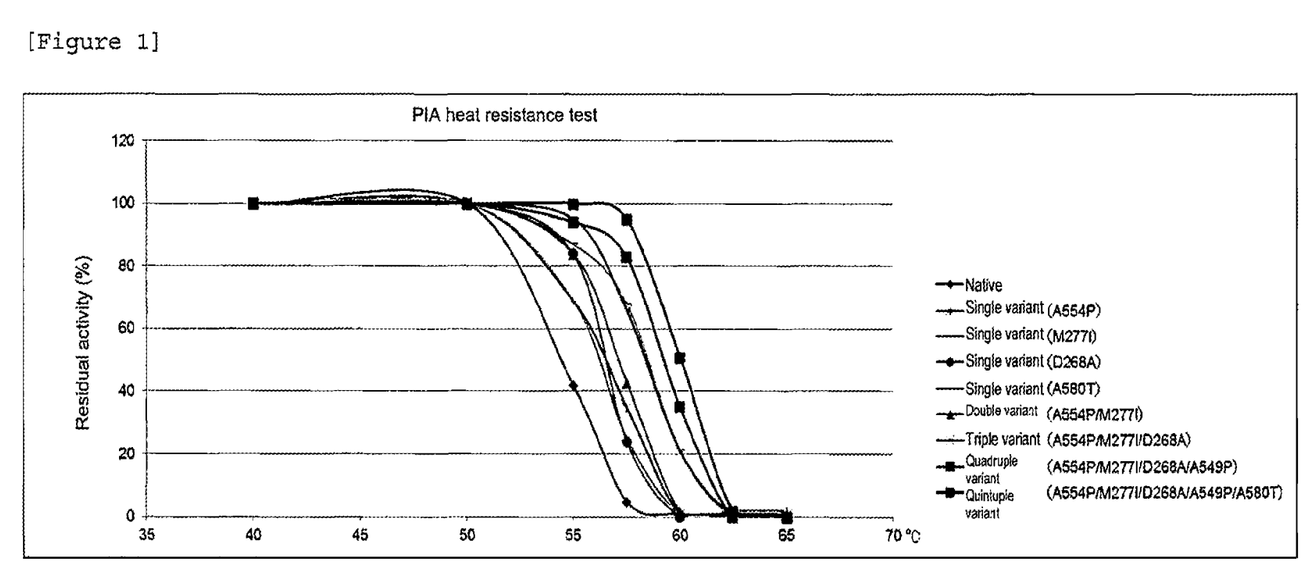
FIG. 1 is a graph showing the thermal stability of native enzyme and enzyme variants.

As a result, as shown in FIG. 1 and Table 1, it was found that the improvement in the degree of heat resistance was verifies as follows: that of the single variant (A554P) is about 1.2° C., that of the single variant (M277I) is about 1.1° C., that of the single variant (D268A) is about 1.3° C., that of the single variant (A580T) is about 4.5° C., that of the double variant (A554P/M277I) is about 3.2° C., that of the triple variant (A554P/M277I/D268A) is about 4.3° C., that of the quadruple variant (A554P/M277I/D268A/A549P) is about 5.1° C., and that of the quintuple variant (A554P/M277I/D268A/A549P/A580T) is about 6° C.

Example 4

Saccharification of Starch

As saccharification of starch, a reducing sugar release test was carried out. To a 10 mM acetate buffer (pH 4.5), soluble starch was added so as to obtain a concentration of 30% (weight/weight) and dissolved by heating. (1) Samples each containing 20 mg of a 0.05 mg/mL glucoamylase (manufactured by Wako Pure Chemical Industries, Ltd.) solution per 30% soluble starch (1 g) and 125 U of the native acid-resistant isoamylase per 300 soluble starch (1 g); (2) Samples each containing 20 mg of glucoamylase per 30% soluble starch (1 g) and 125 U of the quadruple variant isoamylase per 30% soluble starch (1 g); and (3) Samples each containing 20 mg of glucoamylase per 30% soluble starch (1 g) and 125 U of the quintuple variant isoamylase per 30% soluble starch (1 g) were prepared. These samples were separately reacted at 55° C., 60° C. and 62.5° C. for 16 hours.

These samples were heated at 100° C. for 5 minutes to terminate the reaction and the amount of reducing sugar produced was measured by a DNS (3,5-dinitrosalicylic acid) method.

<Measuring Method>

A method for measuring the amount of reducing sugar is as follows:

To a DNS solution (1.5 mL), a diluted sample solution (0.5 mL) was added at an appropriate time, then the mixture was stirred and allowed to react in boiling water for 5 minutes. After the reaction mixture was cooled with water, water (4 mL) was added and the mixture was sufficiently stirred. Absorbance was then measured at 540 nm by a spectrophotometer. The amount of reducing sugar was computationally obtained based on the calibration curve prepared by using a glucose solution. The DNS solution was prepared by dissolving a 4.5% sodium hydroxide solution (1,500 mL) and Rochelle salt (1,275 g) in a 1% DNS solution (4,400 mL), subsequently adding a phenol solution (1% phenol, 2.44% sodium hydroxide) (345 mL) separately prepared and sodium hydrogen carbonate (34.5 g), dissolving them by stirring, storing the solution for 2 days in the dark and filtering the solution through a filter paper, and then put in use.

The results are shown in Table 2. Assuming that the amount of reducing sugar obtained through the reaction using the native acid-resistant isoamylase at 55° C. is 100%, the amount of reducing sugar increased up to 103% when the quadruple variant isoamylase was used and up to 104% when the quintuple variant isoamylase was used. In the reaction at 60° C., the amount of reducing sugar decreased to 98% when the native acid-resistant isoamylase was used; however, the amount was 102% when the quadruple variant isoamylase was used and 104% when the quintuple variant isoamylase was used. Further in the reaction at 62.5° C., the amount of reducing sugar decreased to 97% when the native acid-resistant isoamylase was used; however, the amount was 102% when the quadruple variant isoamylase was used and 103% when the quintuple variant isoamylase was used. Accordingly, it was found that the amount of reducing sugar to be produced increases when the quadruple variant isoamylase was used compared to the native acid-resistant isoamylase. Furthermore, it was found that the amount of reducing sugar to be produced increases when the quintuple variant isoamylase was used compared to the quadruple variant isoamylase. Moreover, it was found that the debranching effect of the native acid-resistant isoamylase reduces as the temperature increases; however, the debranching effect of the quadruple variant isoamylase or quintuple variant isoamylase does not decrease and the yield increases. From this, the thermal stability effect by mutation was verified.

TABLE 1

| Heat resistant variant PIA | Temperature at which residual activity is reduced to half | Degree of heat resistance (° C.) |
|---|---|---|
| Native | 54.1 | 0.0 |
| Single variant (A554P) | 55.3 | 1.2 |
| Single variant (M277I) | 55.2 | 1.1 |
| Single variant (D268A) | 55.4 | 1.3 |
| Single variant (A580T) | 58.6 | 4.5 |
| Double variant (A554P/M277I) | 57.3 | 3.2 |
| Triple variant (A554P/M277I/D268A) | 58.4 | 4.3 |
| Quadruple variant (A554P/M277I/D268A/A549P) | 59.2 | 5.1 |
| Quintuple variant (A554P/M277I/D268A/A549P/A580T) | 60.1 | 6.0 |

TABLE 2

| Isoamylase used | Amount of reducing sugar (%) | | |
|---|---|---|---|
| | 55° C. | 60° C. | 62.5° C. |
| Native | 100 | 98 | 97 |
| Quadruple variant (A554P/M277I/D268A/A549P) | 103 | 102 | 102 |
| Quintuple variant (A554P/M277I/D268A/A549P/A580T) | 104 | 104 | 103 |

*The amount of reducing sugar was indicated by a relative value when measured value of the condition of 55° C. (1) using the native acid-resistant isoamylase is taken as 100%.

[Sequence Listing]

The invention claimed is:

1. An isoamylase, comprising: a double to quintuple mutation selected from the group consisting of D268A, M277I, A549P, A554P and A580T having isoamylase activity in an isoamylase consisting of the amino acid sequence of SEQ ID NO:1, or an isoamylase consisting of the amino acid sequence with at least 90% identity to SEQ ID NO:1 and comprising a double to quintuple mutation selected from the group consisting of D268A, M277I, A549P, A554P and A580T having isoamylase activity.

2. An enzyme composition for saccharification of starch comprising:
the isoamylase of claim 1.

3. The enzyme composition of claim 2, further comprising:
an enzyme selected from the group consisting of β-amylase, α-amylase and glucoamylase.

4. The isoamylase of claim 1, comprising the mutations of A554P/A580T, M277I/A580T, D268A/A580T, A549P/A580T, A554P/M277 I/A580T, A554P/D268A/A580T, A554P/A549P/A580T, M277I/D268A/A580T, D268A/

A549P/A580T, A554P/M277I/D268A/A549P, A554P/D268A/A549P/A580T, A554P/M277I/A549P/A580T, A554P/M277I/D268A/A580T, M277I/D268A/A549P/A580T or A554P/M277I/D268A/A549P/A580T having isoamylase activity in an isoamylase consisting of the amino acid sequence of SEQ ID NO:1 or an isoamylase comprising the mutations of A554P/A580T, M277I/A580T, D268A/A580T, A549P/A580T, A554P/M277I/A580T, A554P/D268A/A580T, A554P/A549P/A580T, M277I/D268A/A580T, D268A/A549P/A580T, A554P/M277I/D268A/A549P, A554P/D268A/A549P/A580T, A554P/M277I/A549P/A580T, A554P/M277I/D268A/A580T, M277I/D268A/A549P/A580T or A554P/M277I/D268A/A549P/A580T having isoamylase activity consisting of the amino acid sequence with at least 90% identity to SEQ ID NO:1.

5. The isoamulase of claim 1, comprising a double to quintuple mutation selected from the group consisting of D268A, M277I, A549P, A554P and A580T in an isoamylase consisting of the amino acid sequence of SEQ ID NO:1.

6. The isoamulase of claim 1, comprising the mutations of A554P/A580T, M277I/A580T, D268A/A580T, A549P/A580T, A554P/M277I/A580T, A554P/D268A/A580T, A554P/A549P/A580T, M277I/D268A/A580T, D268A/A549P/A580T, A554P/M277I/D268A/A549P, A554P/D268A/A549P/A580T, A554P/M277I/A549P/A580T, A554P/M277I/D268A/A580T, M277I/D268A/A549P/A580T or A554P/M277I/D268A/A549P/A580T in an isoamylase consisting of the amino acid sequence of SEQ ID NO:1.

* * * * *